(12) United States Patent
Koh (10) Patent No.: US 12,419,558 B2
(45) Date of Patent: Sep. 23, 2025

(54) APPARATUS AND SYSTEM FOR MEASURING EYELID TENSION

(71) Applicant: Il Hwan Koh, Seongnam-si (KR)

(72) Inventor: Il Hwan Koh, Seongnam-si (KR)

(73) Assignee: Il Hwan Koh, Seongnam-si (KR)

( * ) Notice: Subject to any disclaimer, the term of this patent is extended or adjusted under 35 U.S.C. 154(b) by 706 days.

(21) Appl. No.: 17/771,788

(22) PCT Filed: Sep. 3, 2020

(86) PCT No.: PCT/KR2020/011842
§ 371 (c)(1),
(2) Date: Apr. 25, 2022

(87) PCT Pub. No.: WO2021/085830
PCT Pub. Date: May 6, 2021

(65) Prior Publication Data
US 2022/0369981 A1 Nov. 24, 2022

(30) Foreign Application Priority Data

Oct. 30, 2019 (KR) .................. 10-2019-0136459

(51) Int. Cl.
*A61B 5/22* (2006.01)
*A61B 3/00* (2006.01)
(Continued)

(52) U.S. Cl.
CPC ............ *A61B 5/224* (2013.01); *A61B 3/0083* (2013.01); *A61B 3/10* (2013.01); *A61B 5/6821* (2013.01); *A61B 2034/742* (2016.02)

(58) Field of Classification Search
CPC ......... A61B 5/224; A61B 3/0083; A61B 3/10; A61B 5/6821; A61B 2034/742;
(Continued)

(56) References Cited

U.S. PATENT DOCUMENTS

2002/0049389 A1* 4/2002 Abreu .................. A61B 3/0058
600/318
2007/0273611 A1* 11/2007 Torch ..................... A61B 3/112
345/8
(Continued)

FOREIGN PATENT DOCUMENTS

JP    H08 278456 A1 * 11/1996
JP    H11-128171 A    5/1999
(Continued)

OTHER PUBLICATIONS

Extended European Search Report dated Nov. 24, 2023 in corresponding European Application No. 20883460.6, in 9 pages.
(Continued)

*Primary Examiner* — Mohammed A Hasan
(74) *Attorney, Agent, or Firm* — Knobbe, Martens, Olson & Bear, LLP (57) ABSTRACT

An apparatus for measuring eyelid tension includes: a cylindrical body; a measuring sensor formed on an outer circumferential surface of the body; and a contact part formed at a longitudinal distal end of the body to come into contact with the body of a person to be measured.

13 Claims, 6 Drawing Sheets

(51) Int. Cl.
*A61B 3/10* (2006.01)
*A61B 5/00* (2006.01)
*A61B 34/00* (2016.01)

(58) Field of Classification Search
CPC ... A61B 5/1103; A61B 5/1107; A61B 5/1126; A61B 5/227; A61B 5/6885; A61B 5/6843
USPC .......................................................... 351/205
See application file for complete search history.

(56) References Cited

U.S. PATENT DOCUMENTS

| | | | |
|---|---|---|---|
| 2010/0097573 A1* | 4/2010 | Verdooner | A61B 3/14 |
| | | | 351/206 |
| 2017/0371180 A1* | 12/2017 | Harant | B29D 11/00038 |
| 2018/0235810 A1 | 8/2018 | Peddada et al. | |
| 2020/0121163 A1 | 4/2020 | Takahashi | |
| 2022/0000403 A1* | 1/2022 | Bjerrum | A61B 5/0004 |

FOREIGN PATENT DOCUMENTS

| | | | |
|---|---|---|---|
| JP | 2002-143093 A | | 5/2002 |
| JP | 2008307275 A | * | 12/2008 |
| JP | 2014-033906 A | | 2/2014 |
| KR | 10-2012-0009330 A | | 2/2012 |
| WO | WO 2019/003272 A1 | | 1/2019 |

OTHER PUBLICATIONS

International Search Report mailed Dec. 11, 2020 in International Application No. PCT/KR2020/011842.

* cited by examiner

APPARATUS AND SYSTEM FOR MEASURING EYELID TENSION

The present application is a U.S. national phase application under 35 U.S.C. § 371 of International Application No. PCT/KR2020/011842, filed on Sep. 3, 2020, which claims the benefit of Korean Patent Application No. 10-2019-0136459 filed on Oct. 30, 2019 in the Korean Intellectual Property Office, the entire disclosure of each of which is incorporated herein by reference.

TECHNICAL FIELD

The present disclosure relates to an apparatus for measuring eyelid tension and a system for measuring eyelid tension.

BACKGROUND

An eyeball has an internal pressure that resists an external atmosphere. This internal pressure is called intraocular pressure. A shape of the eyeball may be maintained by the intraocular pressure. For example, the eyeball may have a spherical shape. A cornea surrounds the front of the eyeball. When the cornea has a uniform thickness, there is no problem in maintaining the shape of the cornea. In addition, even though the thickness of the cornea is slightly changed due to a vision correction surgery, when the cornea can sufficiently resist the intraocular pressure, there is no problem in maintaining the functioning shape of the cornea. However, when the intraocular pressure is excessively increased or the resistance of the eyeball (especially, the cornea) is weakened due to various factors, deformation of the eyeball may occur. For example, keratoconus or keratectasia is a disease in which a part of the cornea protrudes in a cone shape and is accompanied by various inconveniences such as decreased both corrected and uncorrected vision.

Practically, a force applied to an eyeball by an upper eyelid rather than a lower eyelid may be considered as a more important factor. However, a degree of influence may vary according to characteristics of an individual eyelid. As such, since an eyelid tension has a direct effect on the eyeball, the eyelid tension may be considered as an important factor in cornea-related vision correction surgery or treatment of corneal-related diseases. The eyelid tension may also increase pressure applied to the eyeball to thereby cause an increase in the intraocular pressure. However, an apparatus capable of objectively measuring the eyelid tension has not been adequately developed, and there is a need for research on how to use a measured value of the eyelid tension.

SUMMARY

Keratectasia is the most serious complication that occurs during LASIK/LASEK surgery. In order to prevent keratectasia, the thickness of the cornea should be thickly secured during surgery. In addition, when the external pressure applied to the eyeball is reduced after surgery, this is also to lower the risk of keratectasia. Therefore, in order to predict the possibility of postoperative keratectasia in advance, it is necessary to measure the eyelid tension of all patients considering LASIK/LASEK surgery.

Apparatuses for measuring eyelid tension that have already been developed are quite large and complex. When an initial setting is slightly wrong, there is a great possibility of an error in a measured value, and it takes a lot of time and effort for a doctor to measure the eyelid tension during treatment.

Various embodiments of the present disclosure provide an apparatus for measuring eyelid tension, which is capable of measuring the eyelid tension of a user by forming a measuring sensor on an outer circumferential surface of a cylindrical body.

An apparatus for measuring eyelid tension according to one embodiment of the present disclosure includes a cylindrical body, a measuring sensor formed on an outer circumferential surface of the body, and a contact part formed at a longitudinal distal end of the body to come into contact with the body of a person to be measured.

In one embodiment, the measuring sensor may include a tension sensor or a pressure sensor formed in a circumferential direction of the body.

In one embodiment, the measuring sensor may be configured to be disposed between an upper eyelid and a lower eyelid of the person to be measured and to measure the eyelid tension of the person to be measured.

In one embodiment, the body may include: a first body at which the measuring sensor is formed; and a second body at which the contact part is formed and which is formed radially inward from the first body.

In one embodiment, a space in which the first body and the second body are spaced apart in a radial direction may be formed between the first body and the second body.

In one embodiment, the apparatus for measuring eyelid tension may further include an air intake which is installed in the space and configured to apply a negative suction pressure to the space.

A system for measuring eyelid tension according to another embodiment of the present disclosure includes: at least one apparatus for measuring eyelid tension; a controller at which the at least one apparatus for measuring eyelid tension is installed; and a mounting apparatus on which the controller is mounted.

In one embodiment, the mounting apparatus may include: an installation part at which the controller is installed; and a joystick configured to control movement of the installation part.

In one embodiment, the controller may include a display configured to display eyelid tension measured by a measuring sensor.

In one embodiment, the body may include: a first body at which the measuring sensor is formed; and a second body at which a contact part is formed and which is formed radially inward from the first body.

In one embodiment, the at least one apparatus for measuring eyelid tension may include a plurality of apparatuses for measuring eyelid tension in which a thickness of the first body is formed to be different for each apparatus.

In one embodiment, in the plurality of apparatuses for measuring eyelid tension, a thickness of the second body may be formed to be the same for each apparatus.

In one embodiment, a space in which the first body and the second body are spaced apart in a radial direction may be formed between the first body and the second body.

In one embodiment, the apparatus for measuring eyelid tension may further include an air intake which is installed in the space and configured to apply a negative suction pressure to the space.

According to embodiments of the present disclosure, in order to overcome the problems of the above-described conventional method, the eyelid tension, which includes a blinking force and a muscle tone in a basic static state of an orbicularis oculi muscle constituting the eyelids, can be evaluated by measuring an amount of force required during closing of the eyelids.

According to embodiments of the present disclosure, a process of mounting the apparatus for measuring eyelid tension on the eye is very simple. Without much influence from movement of a head or a body of a patient (for example, when the head or the body of the patient moves excessively, suction of an attaching part may be easily released to prevent occurrence of damage to an eyeball), it is possible to solve the problem that the eyelid tension measured according to the conventional method reflects only a part of the eyelid. It is possible to considerably improve reproducibility or reliability of a measured value of the eyelid tension.

According to embodiments of the present disclosure, since the eyelid tension can be objectively evaluated, it is possible to improve effectiveness of diagnosis and treatment of keratoconus, keratectasia, and regular and irregular astigmatism which are greatly affected by the eyelid tension.

DETAILED DESCRIPTION

Embodiments of the present disclosure are shown for the purpose of explaining the technical idea of the present disclosure. The scope of rights according to the present disclosure is not limited to the embodiments presented below or the detailed descriptions of such embodiments.

All technical terms and scientific terms used in the present disclosure have the meaning generally understood by those of ordinary skill in the art to which the present disclosure pertains, unless otherwise defined. All terms used in the present disclosure are chosen for the purpose of more clearly describing the present disclosure and are not chosen to limit the scope of rights according to the present disclosure.

As used in the present disclosure, expressions such as "comprising," "including," "having," and the like are to be understood as open-ended terms having the possibility of encompassing other embodiments, unless mentioned otherwise with respect to the phrase or sentence containing such expressions.

The singular expressions that will be described in the present disclosure may encompass plural expressions unless otherwise stated, which also applied to the singular expressions in the claims.

The expressions such as "first," "second," etc., which are shown in the present disclosure are used to distinguish a plurality of elements from one another, and are not intended to limit the order or importance of the corresponding elements.

The expression "based on" used herein is used to describe one or more factors that influence actions of a decision, a determination, or an operation described in a phrase or sentence including the relevant expression, and this expression does not exclude an additional factor influencing the decision, the action of determination, or the operation.

When a certain component is described herein as "coupled to" or "connected to" another component, this should be understood as meaning that the certain component may be directly coupled or connected to the another component or that the certain component may be coupled or connected to the other component via a new intervening component.

Hereinafter, embodiments of the present disclosure will be described with reference to the accompanying drawings. In the accompanying drawings, the like or relevant components are indicated by like reference numerals. In the following description of embodiments, repeated descriptions of the identical or relevant components will be omitted. However, even if the descriptions of components are omitted, such components are not intended to be excluded in an embodiment.

Figure 1:
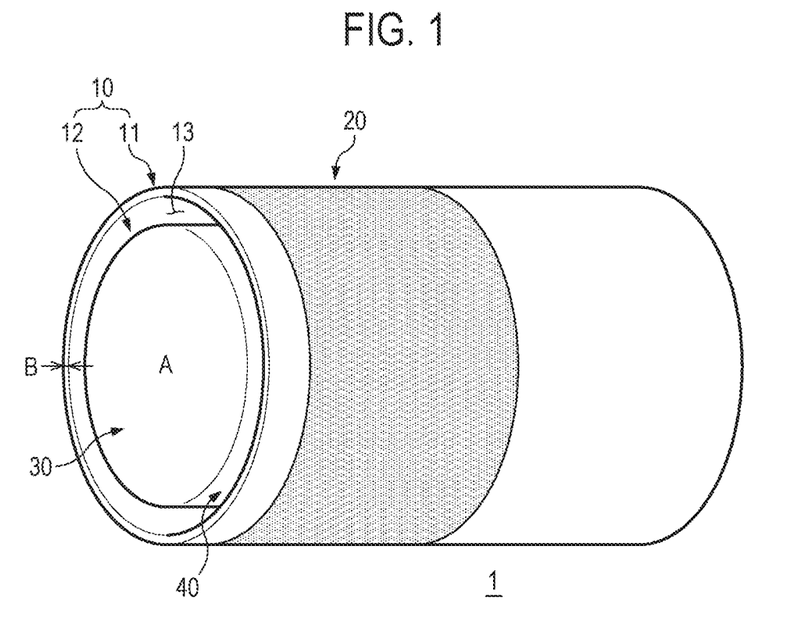
FIG. 1 is a perspective view illustrating an apparatus for measuring eyelid tension according to one embodiment of the present disclosure.

FIG. 1 is a perspective view illustrating an apparatus 1 for measuring eyelid tension according to one embodiment of the present disclosure.

The apparatus 1 for measuring eyelid tension may include a body 10, a measuring sensor 20 formed on an outer circumferential surface of the body 10, and a contact part 30 formed at a longitudinal distal end of the body 10.

The body 10 may have a cylindrical shape. The body 10 may include a first body 11 at which the measuring sensor 20 is formed and a second body 12 at which the contact part 30 is formed and which is formed radially inward from the first body 11. The contact part 30 may be formed on a distal end surface of the second body 12. Meanwhile, based on the longitudinal direction, a distal end surface of the first body 11 and the distal end surface of the second body 12 may be formed at the same position (that is, on the same plane at the same height).

The measuring sensor 20 may be provided as, for example, a tension sensor or a pressure sensor. The measuring sensor 20 may be formed in a circumferential direction of an outer circumferential surface of the first body 11. The measuring sensor 20 may be configured to come into direct contact with an upper eyelid and a lower eyelid of a person to be measured.

A space 13 in which the first body 11 and the second body 12 are spaced apart in a radial direction may be formed between the first body 11 and the second body 12. An air intake 40 may be disposed in the space 13. The air intake 40 may be configured to induce an airflow so that air flows toward the contact part 30 based on the longitudinal direction. That is, the air intake 40 may suction a marginal zone of the cornea/conjunctiva of the person to be measured through a negative suction pressure. In this case, a flat portion of the contact part 30 comes into contact with the cornea of the person to be measured, so that the apparatus 1 for measuring eyelid tension may be fixed to the eyeball of the person to be measured.

Figure 2:
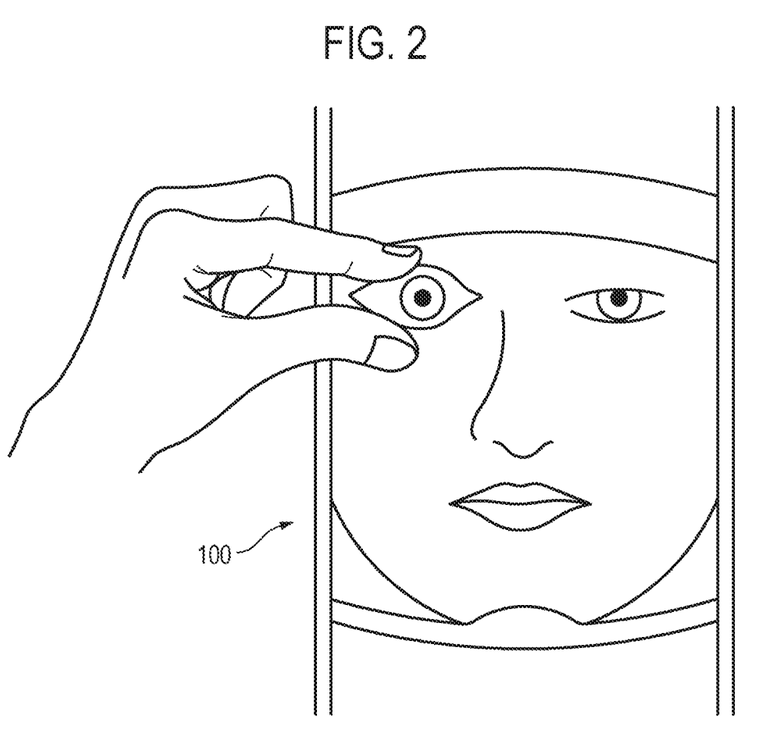
FIG. 2 illustrates a state in which a process of bringing an apparatus for measuring eyelid tension according to one embodiment of the present disclosure into contact with an eyeball of a person to be measured is viewed from in front of the person to be measured.
Figure 3:
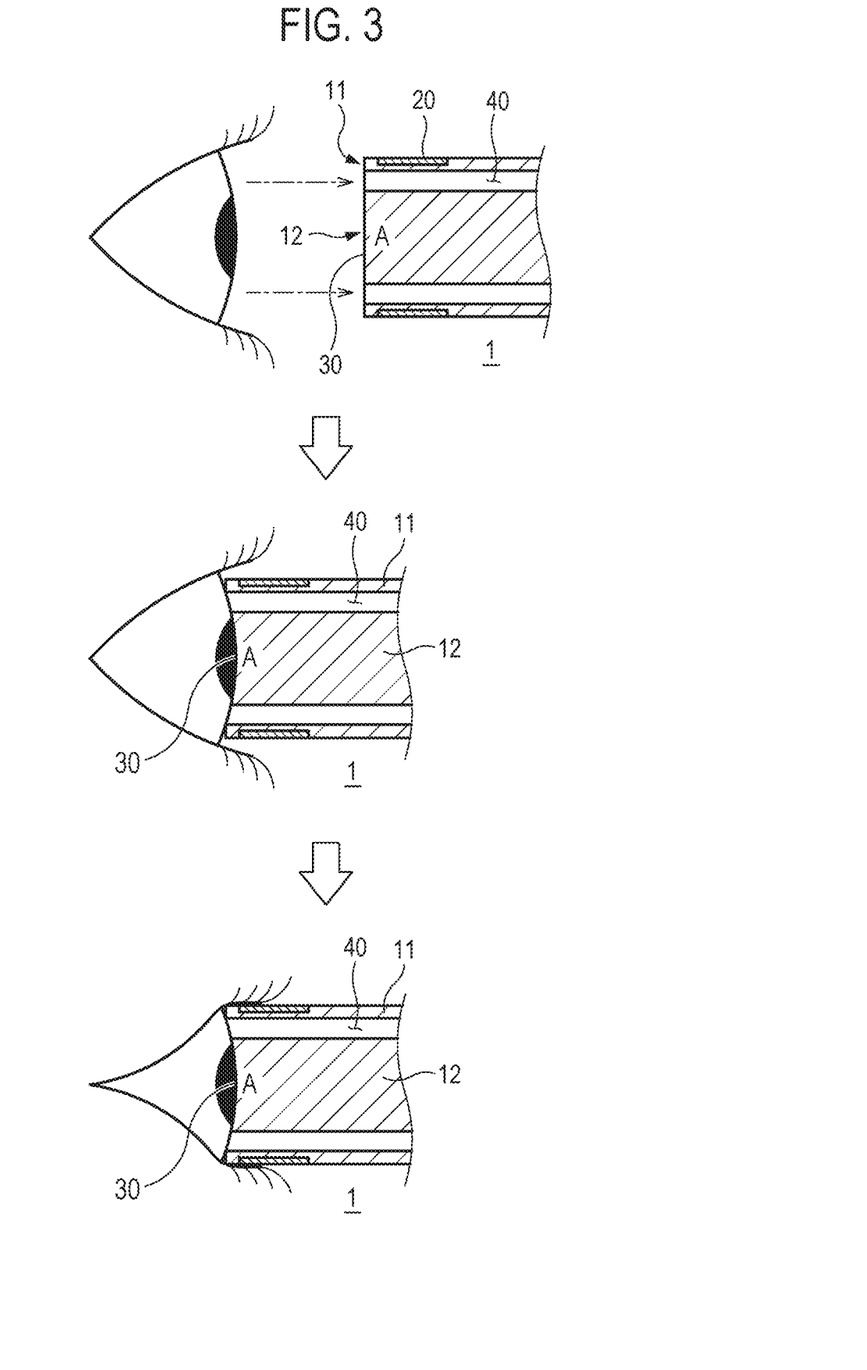
FIG. 3 illustrates a state in which a process of bringing an apparatus for measuring eyelid tension according to one embodiment of the present disclosure into contact with an eyeball of a person to be measured is viewed from a side of the person to be measured.

FIG. 2 illustrates a state in which a process of bringing the apparatus 1 for measuring eyelid tension according to one embodiment of the present disclosure into contact with the eyeball of the person to be measured is viewed from in front of the person to be measured. FIG. 3 illustrates a state in which the process of bringing the apparatus 1 for measuring eyelid tension according to one embodiment of the present disclosure into contact with the eyeball of the person to be measured is viewed from a side of the person to be measured.

Referring to FIGS. 2 and 3, first, the face of the person to be measured is brought into contact with a mounting apparatus 100, and then the eyelids of the person to be measured are opened by hand of a measurer. Next, in a direction in which the contact part 30 of the apparatus 1 for measuring eyelid tension faces the eyeball of the person to be measured, the apparatus 1 for measuring eyelid tension is disposed so that the contact part 30 is adjacent to the cornea of the eyeball. Next, when the air intake 40 configured to suction air into the space between the first body 11 and the second body 12 is operated, the contact part 30 comes into contact with the cornea of the eyeball. In this situation, when the measurer removes his or her hand from the eyelids of the person to be measured and the person to be measured closes the eye, the upper eyelid and the lower eyelid come into contact with the measuring sensor 20 and press the measuring sensor 20.

Figure 4:
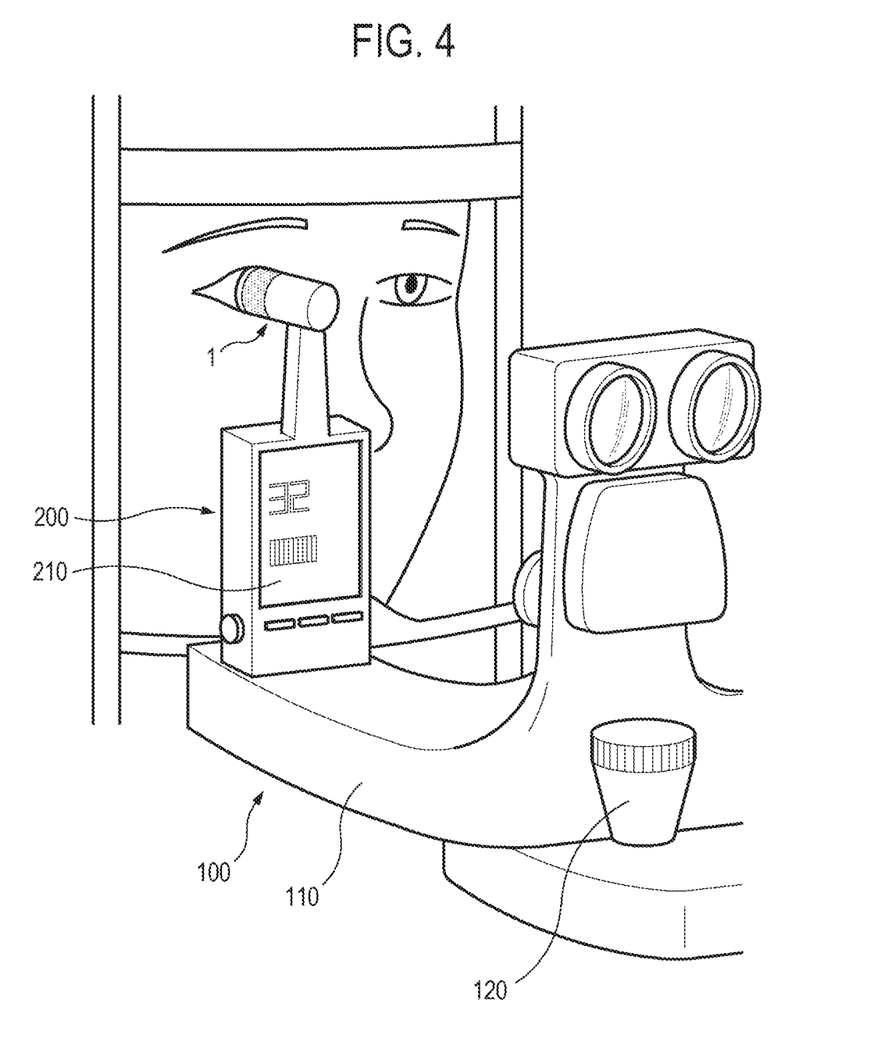
FIG. 4 is a perspective view illustrating a state in which an apparatus for measuring eyelid tension according to one embodiment of the present disclosure is installed at a mounting apparatus.

FIG. 4 is a perspective view illustrating a state in which the apparatus 1 for measuring eyelid tension according to one embodiment of the present disclosure is installed at the mounting apparatus 100. The apparatus 1 for measuring eyelid tension may be installed at a controller 200. The controller 200 may be installed at the mounting apparatus 100. The mounting apparatus 100 may have the shape of, for example, a slit lamp microscope. In this embodiment, a system for measuring eyelid tension may be understood as including the apparatus 1 for measuring eyelid tension, the controller 200, and the mounting apparatus 100.

The mounting apparatus 100 may include an installation part 110 at which the controller 200 is installed and a joystick 120 configured to control movement of the installation part 110. The joystick 120 may control movement of the installation part 110 in forward, rearward, and leftward/rightward directions. The installation part 110 may be moved in an upward/downward direction when the joystick 120 is turned.

The controller 200 may be designed to be attachable to and detachable from the installation part 110. On the other hand, in order to be similar to the slit lamp microscope, the controller 200 may be manufactured integrally with the installation part 110. However, even in this case, the joystick 120 configured to control movement of the installation part 110 using a principle similar to that of the slit lamp microscope may be provided to be able to move and finely adjust the installation part 110 in upward/downward and leftward/rightward directions.

The controller 200 may include a display 210 configured to display the eyelid tension measured by the apparatus 1 for measuring eyelid tension.

The controller 200 may be connected by a wire to an external analysis apparatus (not shown) (e.g., a computer) to transmit eyelid tension data measured through the apparatus 1 for measuring eyelid tension to the external analysis apparatus (not shown).

As another example, a wireless communication module (not shown) may be installed within the controller 200. The wireless communication module (not shown) may transmit the eyelid tension data measured through the apparatus 1 for measuring eyelid tension to the external analysis apparatus (not shown) using Bluetooth or Wi-Fi.

Figure 5:
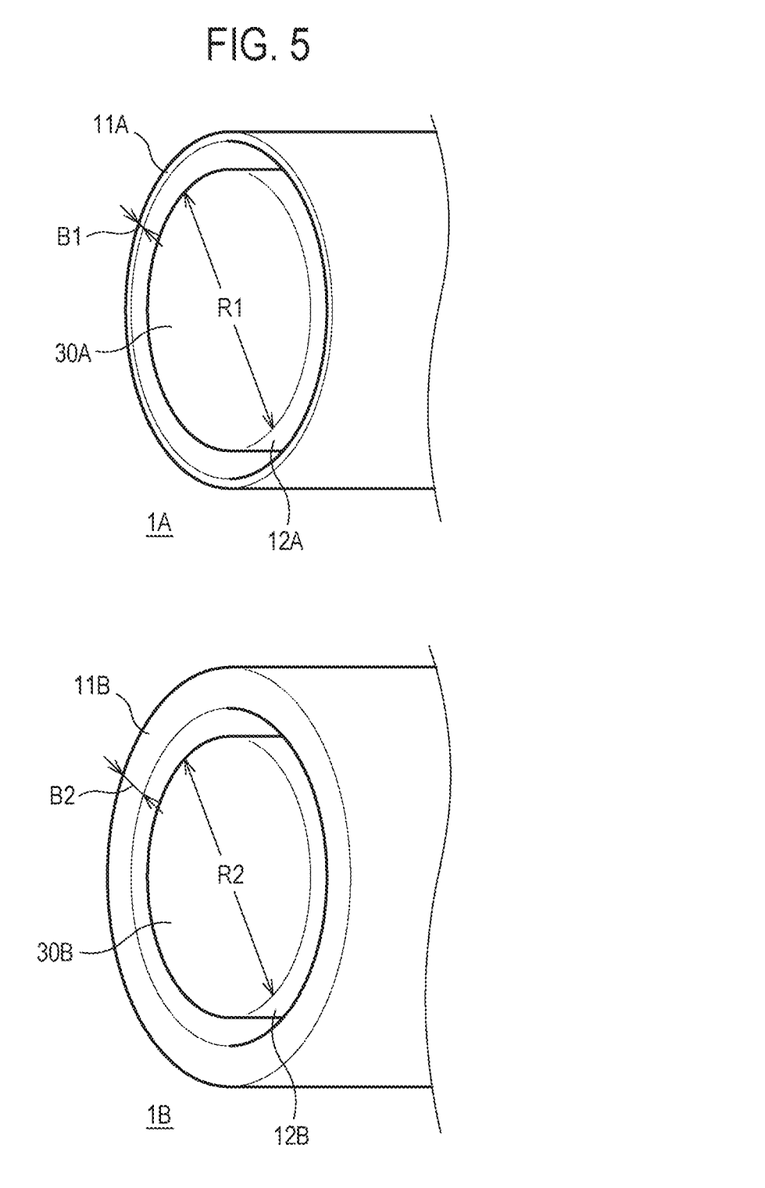
FIG. 5 is a perspective view illustrating apparatuses for measuring eyelid tension that have diameters of different sizes.

FIG. 5 is a perspective view illustrating apparatuses 1A and 1B for measuring eyelid tension that have diameters of different sizes.

A thickness B1 of a first body 11A of the apparatus 1A for measuring eyelid tension that is illustrated at the upper side in FIG. 5 may be formed to be different from a thickness B2 of a first body 11B of the apparatus 1B for measuring eyelid tension that is illustrated at the lower side in FIG. 5. Referring to FIG. 5, the thickness B2 may be formed to be larger than the thickness B1. In addition, here, sizes of second bodies 12A and 12B may be identical to each other.

In this way, when the thicknesses B1 and B2 are formed to be different from each other while diameters R1 and R2 of the second bodies 12A and 12B are configured to be the same, it is possible to compensate for individual differences in the palpebral fissure (the opening degree between the upper eyelid and lower eyelid in daily life). That is, the first body 11B having the thickness B2 may be chosen for a person who inherently has a relatively large palpebral fissure size. The first body 11A having the thickness B1 may be chosen for a person who has a relatively small palpebral fissure size.

However, chosen sizes of apparatuses for measuring eyelid tension for different sizes of the human palpebral fissure may vary according to determination of the measurer. Accordingly, a thickness B of the first body 11 may be set to three sizes of B1, B2, and B3, and then for each person to be measured, three pieces of eyelid tension data may be obtained by measuring eyelid tension using the first bodies 11 of the three different thicknesses. A pattern may be analyzed based on the three pieces of eyelid tension data.

On the other hand, the eyelid tension may be measured by applying a thickness B of an appropriate size and setting only one thickness that enables eyelid tension measurement for all persons to be measured. In this case, an option for measuring eyelid tension of a person to be measured one time may be chosen by adjusting the size of the thickness B appropriately.

Meanwhile, referring to FIG. 3, contact parts 30A and 30B may be formed as a flat surface. However, the contact part may also be formed as a curved surface of a concave shape to fit the shape of the cornea and make better contact with the cornea (that is, to better adhere to the cornea).

Figure 6:
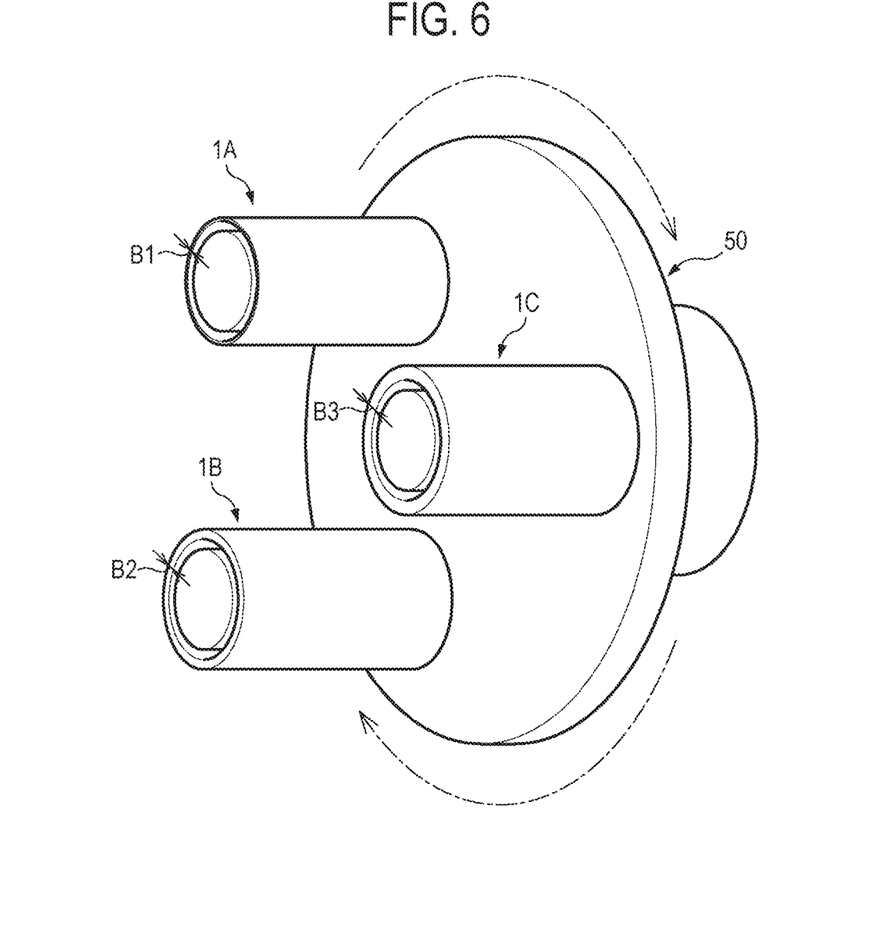
FIG. 6 is a perspective view illustrating a state in which apparatuses for measuring eyelid tension that have diameters of different sizes are installed at a rotating coupling part.

FIG. 6 is a perspective view illustrating a state in which apparatuses 1A, 1B, and 1C for measuring eyelid tension that have diameters of different sizes are installed at a rotating coupling part 50.

The rotating coupling part 50 illustrated in FIG. 6 may have, for example, a flange shape. An outer side surface of the flange shape may have a circular shape. Here, the apparatuses 1A, 1B, and 1C for measuring eyelid tension that have three different sizes B1, B2, and B3 may be disposed to be spaced apart in a circumferential direction of a disk.

Referring to FIG. 4, the rotating coupling part 50 to which the apparatuses 1A, 1B, and 1C for measuring eyelid tension are coupled may be installed at the controller 200. Each of the apparatuses 1A, 1B, and 1C for measuring eyelid tension may be electrically connected to the controller 200.

In the case where it is necessary to use the plurality of apparatuses 1A, 1B, and 1C for measuring eyelid tension, when the rotating coupling part 50 is not present, the apparatuses 1A, 1B, and 1C for measuring eyelid tension have to be replaced for use at the controller 200 each time. However, according to an embodiment illustrated in FIG. 6, by rotating the rotating coupling part 50 in an axial direction, each of the apparatuses 1A, 1B, and 1C for measuring eyelid tension may be selectively used as necessary.

Although the present disclosure has been described heretofore with reference to some embodiments and examples shown in the accompanying drawings, it should be noted that there may be various substitutions, modifications, and changes without departing from the technical idea and scope of the present disclosure, which can be understood by those skilled in the technical field to which the present disclosure pertains. In addition, such substitutions, modifications, and changes should be construed to belong to the scope of the claims appended herein.

What is claimed is:

1. An apparatus for measuring eyelid tension, comprising:
   a cylindrical body;
   a measuring sensor formed on an outer circumferential surface of the body and configured to be disposed between an upper eyelid and a lower eyelid of a person to be measured to measure the eyelid tension such that the upper eyelid and the lower eyelid come into contact with the measuring sensor and press the measuring sensor; and
   a contact part formed at a longitudinal distal end of the body to come into contact with an eyeball of the person to be measured between the upper eyelid and the lower eyelid.

2. The apparatus of claim 1, wherein the measuring sensor includes a tension sensor or a pressure sensor formed in a circumferential direction of the body.

3. The apparatus of claim 1, wherein the body includes:
   a first body at which the measuring sensor is formed; and
   a second body at which the contact part is formed and which is formed radially inward from the first body.

4. The apparatus of claim 3, wherein a space in which the first body and the second body are spaced apart in a radial direction is formed between the first body and the second body.

5. The apparatus of claim 4, further comprising an air intake which is installed in the space and configured to apply a negative suction pressure to the space.

6. A system for measuring eyelid tension, comprising: at least one apparatus for measuring eyelid tension of claim 1,
   a controller at which the at least one apparatus for measuring an eyelid tension is installed; and
   a mounting apparatus on which the controller is mounted.

7. The system of claim 6, wherein the mounting apparatus includes:
   an installation part at which the controller is installed; and
   a joystick configured to control movement of the installation part.

8. The system of claim 6, wherein the controller includes a display configured to display the eyelid tension measured by the measuring sensor.

9. The system of claim 6, wherein the body includes:
   a first body at which the measuring sensor is formed; and
   a second body at which the contact part is formed and which is formed radially inward from the first body.

10. The system of claim 9, wherein the at least one apparatus for measuring eyelid tension includes a plurality of apparatuses for measuring eyelid tension in which a thickness of the first body is formed to be different for each apparatus.

11. The system of claim 10, wherein, in the plurality of apparatuses for measuring eyelid tension, a thickness of the second body is formed to be the same for each apparatus.

12. The system of claim 9, wherein a space in which the first body and the second body are spaced apart in a radial direction is formed between the first body and the second body.

13. The system of claim 12, wherein the apparatus for measuring eyelid tension further comprises an air intake which is installed in the space and configured to apply a negative suction pressure to the space.

* * * * *